United States Patent [19]

Dirlikov

[11] Patent Number: 4,663,416

[45] Date of Patent: May 5, 1987

[54] NOVEL CONDENSATION POLYMERS CONTAINING UNITS FROM 8,9-BIS(HYDROXYALKYL)-EXO-3,4,5-TRI-THIATRICYCLO[5.2.1.0$^{2,6}$]DECANE

[75] Inventor: Stoil K. Dirlikov, Midland, Mich.

[73] Assignee: The Dow Chemical Company, Midland, Mich.

[21] Appl. No.: 846,540

[22] Filed: Mar. 31, 1986

[51] Int. Cl.$^4$ ............................................. C08G 18/38
[52] U.S. Cl. ..................................... 528/73; 528/103; 528/109; 528/294; 549/31
[58] Field of Search ................. 528/73, 103, 109, 294; 549/31

[56] References Cited

U.S. PATENT DOCUMENTS

| | | | |
|---|---|---|---|
| 3,088,935 | 5/1963 | Krespan | 260/79 |
| 3,164,643 | 1/1965 | Hubbard | 260/830 |
| 3,338,874 | 8/1967 | Costanza | 260/79 |
| 3,499,863 | 3/1970 | Kutch | 260/31.6 |
| 3,586,700 | 6/1971 | Kurtz et al. | 260/327 |
| 3,631,158 | 12/1971 | Esclamadon et al. | 260/79 R |
| 4,033,982 | 7/1977 | Hay | 260/327 |
| 4,067,842 | 1/1978 | Braden | 260/31.6 |
| 4,474,970 | 10/1984 | Dirlikov | 549/31 |

Primary Examiner—Maurice J. Welsh

[57] ABSTRACT

Novel condensation polymers are of the unit formula

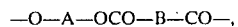

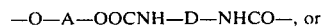

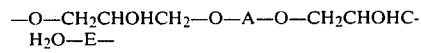

wherein A is the residue of a substituted or unsubstituted 8,9-bis(hydroxyalkyl)-exo-3,4,5-trithiatricyclo[5.2.1.0$^{2,6}$]decane of the formula

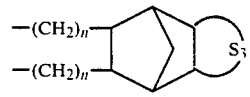

B is the residue of a substituted or unsubstituted aliphatic, cycloaliphatic or aromatic dicarboxylic acid; D is the residue of a substituted or unsubstituted aliphatic, cycloaliphatic or aromatic diisocyanate; E is the residue of a substituted or unsubstituted aliphatic, cycloaliphatic or aromatic dihydroxylic chain extender for a diglycidyl ether of the trithiatricyclo[5.2.1.0$^{2,6}$]decane and n is 1–10.

22 Claims, No Drawings

NOVEL CONDENSATION POLYMERS CONTAINING UNITS FROM 8,9-BIS(HYDROXYALKYL)-EXO-3,4,5-TRITHIA-TRICYCLO[5.2.1.0²,⁶]DECANE

TECHNICAL FIELD

This invention relates to condensation polymers, derived from 8,9-bis(hydroxyalkyl)-exo-3,4,5-trithiatricyclo[5.2.1.0²,⁶]decane compounds. More particularly, this invention relates to polyesters, polyurethanes and epoxy polymer compositions containing a trithiatricyclo moiety in the main polymer chain.

The polymers of this invention are characterized by lower water absorption than that of corresponding polymers, containing no sulfur. The polymers can be crosslinked through the sulfur rings of the 3,4,5-trithiatricyclo[5.2.1.0²,⁶]decane units.

SUMMARY OF THE INVENTION

Novel condensation polymers are of the generic unit formula

—O—A—OCO—B—CO—,

—O—A—OOCNH—D—NHCO—, or

—O—CH$_2$CHOHCH$_2$—O—A—O—CH$_2$CHOHCH$_2$O—E—, wherein A is the residue of a substituted or unsubstituted 8,9-bis(hydroxyalkyl)exo-3,4,5-trithiatricyclo[5.2.1.0²,⁶]decane of the formula

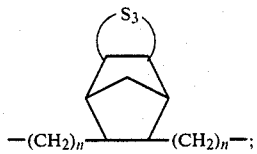

B is the residue of a substituted or unsubstitued aliphatic, cycloaliphatic or aromatic carboxylic acid; D is the residue of a substituted or unsubstituted aliphatic, cycloaliphatic or aromatic diisocyanate; E is the residue of a substituted or unsubstituted aliphatic, cycloaliphatic or aromatic dihydroxylic chain extender for a diglycidyl ether of the trithiatricyclo[5.2.1.0²,⁶]decane and n is 1–10.

DETAILED DESCRIPTION OF THE ILLUSTRATIVE EMBODIMENTS 3,4,5-Trithiatricyclodecane compounds are known. Representative compounds of the series have been disclosed by Kurtz et al. (U.S. Pat. No. 3,586,700), Hay (U.S. Pat. No. 4,033,982) and Dirlikov (U.S. Pat. No. 4,474,970), all herein incorporated by reference.

The trithiatricyclo compounds are prepared by reaction between precursor norbornylene compounds and sulfur in the presence of a sulfide catalyst, such as sodium sulfide. A representative diol, used in making polymers of this invention, is 8,9-bis(hydroxymethyl)-exo-3,4,5-trithiatricyclo[5.2.1.0²,⁶]decane, which is of the formula,

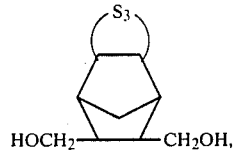

that is, a compound corresponding to A, wherein n is 1. Preferred sulfide catalysts are sodium, ilithium or potassium sulfides.

The compound, or corresponding compounds based on substituted norbornylene precursors, is made by condensation of maleic anhydride and cyclopentadiene to form nadic anhydride, endo-bicyclo[2.2.1]hept-5-ene-2,3-dicarboxylic anhydride, which is reduced to 5,6-bis(hydroxymethyl)bicyclo[2.2.1]hept-2-ene. This compound is sulfurized to a corresponding trithiatricyclo compound, as represented by the equations:

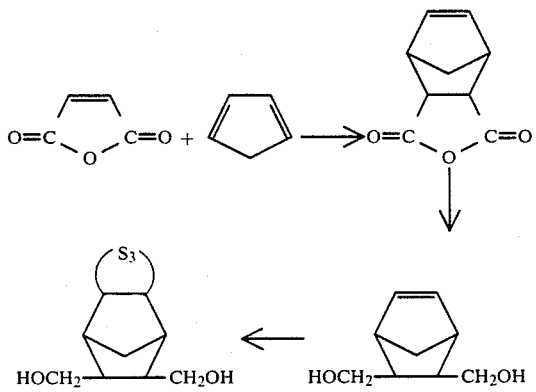

It will be understood that other diols, included within the definition of "substituted or unsubstituted trithiatricyclo[5.2.1.0²,⁶]decane" can be prepared by sulfurization of a condensation product of an appropriately-substituted cyclopentadiene and appropriately-substituted monoolefin. The trithiatricyclodecane compounds can therefore be based, for sake of illustration, on condensation products of cyclopentadiene, alkylcyclopentadienes, halocyclopentadienes, arylcyclopentadienes, cycloalkylcyclopentadienes and the like. The olefin condensed with the cyclopentadiene can be selected from among unsaturated glycols, so as to provide an intermediate in which n has the desired number of carbon atoms. Alternatively, the cyclopentadiene can be condensed with an unsaturated dicarboxylic acid, e.g., 2-octenedioic acid, and the product reduced to the corresponding glycol.

In one aspect, this invention relates to a method for the synthesis of 8,9-bis(hydroxymethyl)-exo-3,4,5-trithiatricyclo[5.2.1.0²,⁶]decanes, wherein an anhydride is prepared from a substituted or unsubstituted cyclopentadiene by reaction with maleic anhydride, reduced to a corresponding glycol and sulfurized to a corresponding trithiatricyclodecane. The 8,9-bis(hydroxymethyl)-exo-3,4,5-trithiatricyclo[5.2.1.0²,⁶]decane members of the series are therefore preferred for incorporation into condensation polymers of this invention.

In a further aspect, the polymers of this invention comprise polyesters, which correspond to the generic formula, wherein B is the residue of a substituted or unsubstituted aliphatic, cycloaliphatic or aromatic dicarboxylic acid.

Dicarboxylic aliphatic acids include, but are not limited to, oxalic acid, malonic acid, succinic acid, glutaric acid, 2-butyl-2-ethylglutaric acid, 2,3-diethylsuccinic acid, 2,2-dimethylmalonic acid, adipic acid, pimelic acid, suberic acid, azelaic acid, sebacic acid, decanedioic acid, undecanedioic acid, dodecanedioic acid, tetradecanedioic acid, hexadecanedioic acid, octadecanedioic acid and docosanedioic acid, including branched structures, containing the desired number of carbon atoms. Preferred diacids for making the aliphatic polyesters of this invention are those having 6–14 methylene groups. Preferred polymers are those derived from 8,9-bis(hydroxymethyl)trithiatricyclo[5.2.1.0$^{2,6}$]decane. Preferred polyesters of this invention are therefore those having the unit formula

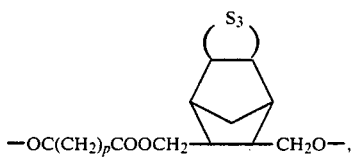

—OC(CH$_2$)$_p$COOCH$_2$———CH$_2$O—, wherein p is 6–14.

Other polyesters of this invention comprise those obtained by reaction between a trithiatricyclo glycol and a mono-, di- or tricyclic aromatic dicarboxylic acid. These acids include, but are not limited to, phthalic acid, isophthalic acid, terephthalic acid, various methylphthalic acids, naphthalic acid and other naphthalene dicarboxylic acids, and anthracene dicarboxylic acids. Preferred aromatic esters are those derived from phthalic, isophthalic or terephthalic acids and the trithiatricyclo glycol in which n is 1. These preferred aromatic polyesters can be represented by the unit formula

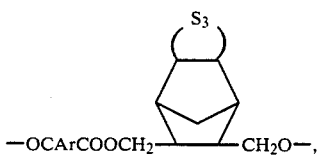

—OCArCOOCH$_2$———CH$_2$O—, wherein Ar is the residue of phthalic, isophthalic or terephthalic acid.

Polyesters can also be made from cycloaliphatic dicarboxylic acids, of which cyclobutane dicarboxylic acid, cyclopentane dicarboxylic acid, the isomeric cyclohexane dicarboxylic acids and the various decahydronaphthalene dicarboxylic acids are representative.

The polyesters can be made by methods well known in the art, including transesterification of the bis(hydroxyalkyl)trithiatricyclodecane with a corresponding methyl or ethyl ester of the dicarboxylic acid or reaction between the bis(hydroxyalkyl)trithiatricyclodecane and an acid halide of the selected dicarboxylic acid. It will normally be preferred to use approximately equimolar amounts of bis(hydroxyalkyl)trithiatricyclodecane and diacid reactant to achieve a product of maximum molecular weight.

The polyesters can also be used as the glycol component of a polyurethane. In this case, it will be preferred to use an excess of the bis(hydroxyalkyl)trithiatricyclodecane, so as to leave available hydroxyl functions for chain extension with a diisocyanate or triisocyanate.

The polyesters of this invention have a reactive trithia function, which is available for crosslinking. Crosslinking can be accomplished by treating the polyester as described in Example 17 of Kurtz et al., U.S. Pat. No. 3,586,700, supra. It is proposed that thus-crosslinked polyesters have the unit formula

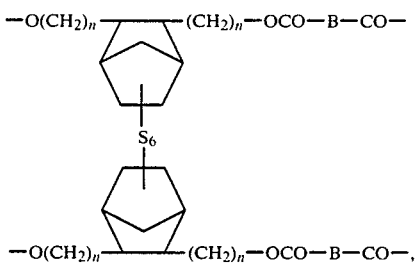

—O(CH$_2$)$_n$———(CH$_2$)$_n$—OCO—B—CO—, wherein the trithiatricyclo[5.2.1.0$^{2,6}$]decane is substituted or unsubstituted.

In another aspect, the polymers of this invention comprise polyurethanes, corresponding to the generic formula, wherein D is the residue of a substituted or unsubstituted aliphatic, cycloaliphatic or aromatic diisocyanate.

the polyurethanes include those based on substituted or unsubstituted aliphatic diisocyanates of 4–20 carbon atoms. Aliphatic diisocyanates include, but are not limited to, tetramethylene diisocyanate, pentamethylene diisocyanate, hexamethylene diisocyanate, octamethylene diisocyanate, decamethylene diisocyanate, undecamethylene diisocyanate, dodecamethylene diisocyanate, tetramethylene diisocyanante, 2,2-dimethyltrimethylene diisocyanate, and other branched aliphatic diisocyanates, having the desired number of carbon atoms. Corresponding oxa- and thiaalkylene diisocyanates are also contemplated as being within the scope of aliphatic diisocyanantes.

Preferred aliphatic polyurethanes are those made from linear polyalkylene diisocyanates of 4–12 methylene groups and 8,9-bis(hydroxymethyl)trithiatricyclodecane. Such polyurethanes can be represented by the unit formula

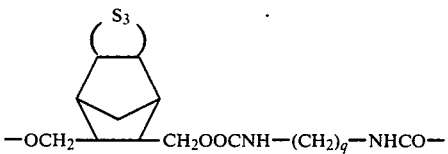

—OCH$_2$———CH$_2$OOCNH—(CH$_2$)$_q$—NHCO— wherein q is 4–12.

Polyurethanes containing an aromatic component include those made from diisocyanates of mono-, di- and tricyclic aromatic compounds. Representative diisocyanates are the various toluene diisocyanates, the phenylene diisocyanates, methylenebis(phenyl isocyanates), naphthalene diisocyanates, anthracene diisocyanates, methylenebis(chlorophenylisocyanates) and the like.

The preferred polyurethanes are those derived from 8,9-bis(hydroxymethyl)trithiatricyclodecane and a toluene diisocyanate, phenylene diisocyanate or methylenebis(phenylisocyanate). These materials can be represented by the unit formula

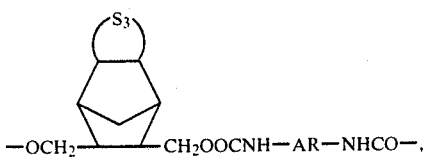

where AR is the residue of toluene diisocyanate, phenylene diisocyanate or methylenebis(phenylisocyanate).

Polyurethanes can also be made from cycloaliphatic diisocyanates, corresponding in general to ring-hydrogenated analogues of the aromatic diisocyanates recited above.

The polyurethanes can further be crosslinked through trithia functional groups in two polymer chains to yield materials thought to have the unit formula

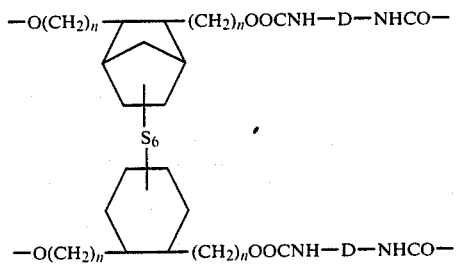

wherein the trithiatricyclo[5.2.1.0$^{2,6}$]decane is substituted or unsubstituted.

The molecular weight of polyurethanes of this invention can be controlled by the ratio of bis(hydroxyalkyl)-trithiatricyclodecane compound to diisocyanate. When it is desired to make high molecular weight polyurethanes, the ratio of reactants should be close to a 1:1 molar ratio. However, in some instances, it may be desirable to produce crosslinked polyurethanes by reaction with a conventional chain extender. In one case, the polyurethanes can be crosslinked by reaction between an available hydroxyl group and a triisocyanate. For this type of reaction, the bis(hydroxyalkyl)trithiatricyclodecane will be used in excess of the diisocyanate to provide the necessary available terminal hydroxyl groups. A triisocyanate useful for this chain extension reaction is a tri- or higher isocyanate, derived from further condensation of diaminodiphenylmethane with formaldehyde and aniline.

The polyurethanes can also be crosslinked by reaction between an available isocyanate group and a triol or triamine. In this case, the diisocyanate will be used in excess of the bis(hydroxyalkyl)trithiatricyclodecane reactant to produce an isocyanated-terminated polymer. Typical triols are glycerol, trimethylol propane, and triethylol propane. Triamines include diethylene triamine and higher polyalkylene polyamines.

In another aspect, the polymers of this invention comprise epoxy compositions, corresponding to the generic formula, wherein E is the residue of a substituted or unsubstituted aliphatic, cycloaliphatic or aromatic dihydroxylic chain extender for a diglycidyl ether of the trithiatricyclo[5.2.1.0$^{2,6}$]decane.

The diglycidyl ether is made in the same fashion as bisphenol A diglycidyl ether and corresponds to the formula

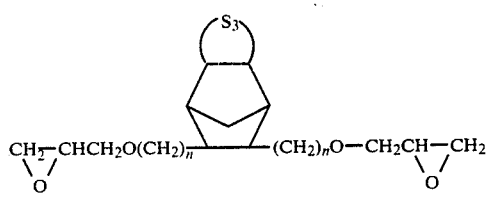

The compositions can be extended or advanced by reaction with any type of dihydroxylic chain extender, including diglycidyl ethers, derived from polypropylene glycol, tetrachlorobisphenol A, bisphenol A, bisphenol F, formaldehyde novolaks, or bis(hydroxyalkyl)trithiatricyclodecane compounds.

Epoxy compositions, chain extended with bis(hydroxyalkyl)trithiatricyclodecanes, will have repeating structures, corresponding to

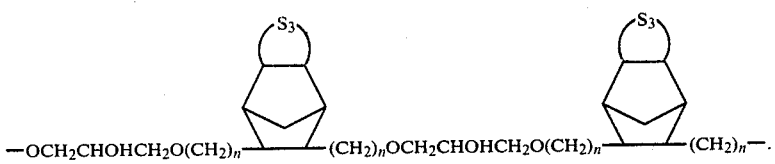

The epoxy compositions, chain extended by bisphenol A, can be represented by the unit formula

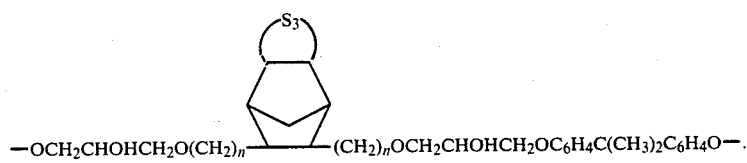

As above, the epoxy compositions can be crosslinked through the trithia substituent to produce materials thought to have the unit formula

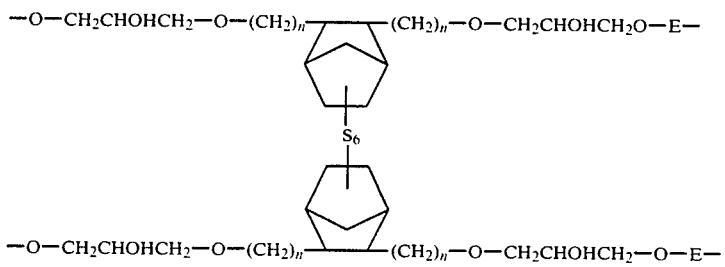

wherein the trithiatricyclo[5.2.1.0$^{2,6}$]decane is substituted or unsubstituted.

Polyepoxy compounds as above can also be cross-linked by reaction with a tri- or polyfunctional amine, for example, diethylenetriamine or triethylenetetramine.

The polymers of this invention could be used to provide light stable compositions, since the trithia function is stable to ultraviolet light. The trithiatricyclodecane monomers can be used as the sole monomer or as a comonomer with other glycols.

The polymers of this invention should form complexes of palladium or platinum with the trithia function. Such polymers should be useful in membrane applications or for separation of palladium, platinum or mercury compounds from other materials.

The polymers of this invention are hydrophobic and absorb less water than corresponding sulfur-free polymers. They are therefore useful for preparing hydrophobic thermoplastic coatings, moldings and the like.

BEST MODE FOR CARRYING OUT THE INVENTION

In a most preferred aspect, the polymers of this invention are polyesters or polyurethanes, derived from 8,9-bis(hydroxymethyl)-exo-2,4,5,-trithiatricyclo[5.2.1.0$^{2,6}$]decane. Most preferred polyesters are those based on aliphatic dicarboxylic acids containing 6–14 methylene groups. Most preferred polyurethanes are those based on polyalkylene diisocyanates of 4–12 methylene groups.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples, temperatures are set forth uncorrected in degrees Celsius. Unless otherwise indicated, all parts and percentages are by weight.

EXAMPLE 1

(a) Reduction of Nadic Anhydride to 5,6-Bis(hydroxymethyl)bicyclo[2.2.1]hept-2-ene To a three-necked flask fitted out with a reflux condenser, Soxhlet extractor, mechanical stirrer and stopper, is charged 500 mL of anhydrous ether and 19.00 g (0.50 mol) of lithium aluminum hydride (Aldrich Chemical Co.). To the thimble of the Soxhlet extractor is charged 41.04 g (0.25 mol) of endo-bicyclo[2.2.1]hept-5-ene-2,3-dicarboxylic acid anhydride (Fluka).

The reduction is carried out by continuous extraction of small portions of the anhydride, which is slightly soluble in ether. The reaction occurs smoothly under stirring and reflux over 20 h. At the end of 20 h, excess lithium aluminum hydride is decomposed by dropwise addition of water. To the reaction mixture, cooled in an ice bath, is added 500 mL of conc (1:1) hydrochloric acid.

The ether and aqueous layers are separated. The aqueous layer is extracted with ether for 8 h in a conventional continuous extraction apparatus. The combined ether extracts are evaporated using a rotating evaporator. The resulting white, crystalline residue is dried under vacuum. The dried product (38.17 g, 99%) melts at 84° C. The product is recrystallized from toluene (10 g in 100 mL of solvent) and dried over phosphorus pentoxide under vacuum at room temperature. The purified product melts at 86° C.

(b) Sulfurization of 5,6-Bis(hydroxymethyl)bicyclo[2.2.1]hept-2-ene

To a 2-L three-necked flask, equipped with stirrer, reflux condenser and nitrogen inlet tube, are charged 96.19 g (3 g-atoms) of sulfur, 161.92 g (1.05 mol) of 5,6-bis(hydroxymethyl)bicyclo[2.2.1]hept-2-ene, 0.59 g (0.0235 mol) of sodium sulfide nonahydrate, 950 mL of pyridine and 50 mL of dimethyformamide. The resulting solution is purged with nitrogen and heated at 110° C. for 48 h.

Solvents are removed from the resulting solution using a rotating evaporator at 45° C. under reduced pressure. A quantitative yield of crude crystalline product is obtained. The product is recrystallized from chloroform (1 g in 50 mL) and dried over phosphorus pentoxide under vacuum at room temperature.

8,9-Bis(hydroxymethyl)-exo-3,4,5-trithiatricyclo[5.2.1.0$^{2,6}$]decane is a yellow crystalline solid which melts at 137°–140° C.

EXAMPLE 2

Polyurethane Prepared from 8,9-Bis(hydroxymethyl)-exo-3,4,5,-trithiatricyclo[5.2.1.0$^{2,6}$]decane and Hexamethylene Diisocyanate The glycol of Example 1 is recrystallized from chloroform, by dissolving 1 g of the glycol in 50 mL of chloroform. The recrystallized material is dried under vacuum.

1,6-Hexamethylene diisocyanate (Polysciences) is distilled through a 10 cm Vigreaux column. The fraction boiling at 127° C. at 10 mm of mercury is used.

N,N-Dimethylacetamide (Aldrich, Gold Label, 99+%) is stored over 3A molecular sieves and used without further purification.

Dibutyl tin dilaurate (Polysciences) is used without further purification.

The polymerization is carried out in a 250-mL four-necked flask, fitted out with a dropping funnel, reflux condenser protected from atmospheric moisture, mechanical stirrer and inlet tube for nitrogen. To a rapidly-stirred solution of 25.04 g (0.1 mol) of 8,9-bis(hydroxymethyl)exo-3,4,5-trithiatricyclo[5.2.1.0²,⁶]decane in 100 mL of dimethylacetamide is added dropwise at room temperature 16.82 g (0.1 mol) of 1,6-hexamethylene diisocyanate. At the end of 2 h, dibutyltin dilaurate (0.2 mL) is added. The resulting mixture is stirred at room temperature for 24 h.

The resulting viscous, transparent solution is diluted with 500 mL of dimethylacetamide and is added dropwise to 5 L of water to precipitate polymer. The resulting suspension is allowed to stand overnight, after which solid product is removed by filtration, washed with water and dried under vacuum at 25° C.

The yield of white polyurethane powder is nearly quantitative.

The polyurethane is soluble in polar solvents, e.g. dimethylacetamide, dimethyl sulfoxide, and dimethylformamide but insoluble in chloroform, carbon tetrachloride or other non-polar solvents.

The product is a flexible thermoplastic with a $T_g = 70°$ C. and $T_{soft} = 165°$ C., determined using a duPont 1090 thermal analyzer and Dennis thermal bar, respectively.

The polyurethane forms films upon evaporation of its solutions. A compression molded specimen made at 100° C. and $1.41 \times 10^7$ Kg/m² is transparent yellow.

Thermal degradation, measured using a duPont 1090 thermal analyzer, began at about 260° C. The thermal stability of this material is higher that that of a polyurethane based on 1,4-cyclohexanedimethanol and m-phenylene diisocyanate.

The polymer is hydrophobic, compared to similar sulfur-free polymers.

EXAMPLE 3

Polyester Prepared from 8,9-bis(hydroxymethyl)-exo-3,4,5-trithiatricyclo[5.2.1.0²,⁶]decane and Sebacoyl Dichloride Sebacoyl dichloride (Aldrich, Gold Label, 99+%) is distilled through a 10 cm Vigreaux column before use. The fraction boiling at 124° C. at 0.5 mm of mercury is used.

Triethylamine (Fluka, puriss. grade) is used without further purification.

Other reagents used are purified as in Example 2.

To a rapidly-stirred solution of 2.50 g (0.01 mol) of 8,9-bis(hydroxymethyl)-exo-3,4,5-trithiatricyclo[5.2.1.0²,⁶]decane in 30 mL of dimethylacetamide, cooled in an ice bath in a flask equipped as in Example 2, is added dropwise 2.39 g (0.01 mol) of sebacoyl dichloride. The addition required about 5 min.

The resulting mixture is stirred at 0° C. for 0.5 h and then at about 60° C. for 8 h. The resulting viscous suspension is added dropwise to 200 mL of water and the suspension is allowed to stand overnight.

The resulting polymer is removed by filtration, washed with several portions of water and dried under vacuum at 50° C. The yield of white powder (4.16 g) is quantitative.

EXAMPLE 4

Diglycidyl Ether of 8,9-Bis(hydroxymethyl)-exo-3,4,5-trithiatricyclo[5.2.1.0²,⁶]decane A mixture of 8,9-bis(hydroxymethyl)-exo-3,4,5-trithiatricyclo[5.2.1.0²,⁶]decane and epichlorohydrin (1:4 molar) in tetrahydrofuran (1 L per mol) is heated and stirred at about 60° C. To the mixture is added solid sodium hydroxide (2 mols per mol of trithiatricyclo compound) at a rate such that reaction mixture remains neutral. The reaction is exothermic and the mixture is cooled to keep the temperature below 60° C. At the end of the reaction, excess epichlorohydrin is removed by distillation. The residue contains the diglycidyl ether and sodium chloride, which is removed by filtration.

The resulting solution/suspension of diglycidyl ether can be used for the preparation of epoxy polymers.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

I claim:

1. A condensation polymer of the unit formula

—O—A—OCO—B—CO—,

—O—A—OOCNH—D—NHCO—, or

—O—CH₂CHOHCH₂—O—A—O—CH₂CHOHCH₂O—E— wherein A is the residue of a substituted or unsubstituted 8,9-bis(hydroxyalkyl)-exo-3,4,5-trithiatricyclo[5.2.1.0²,⁶]decane of the formula

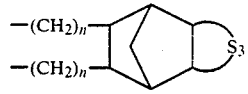

B is the residue of a substituted or unsubstituted aliphatic, cycloaliphatic or aromatic dicarboxylic acid; D is the residue of a substituted or unsubstituted aliphatic, cycloaliphatic or aromatic diisocyanate; E is the residue of a substituted or unsubstituted aliphatic, cycloaliphatic or aromatic dihydroxylic chain extender for a diglycidyl ether of the trithiatricyclo[5.2.1.0²,⁶]decane and n is 1–10.

2. A polymer of claim 1, comprising a polyester, wherein B is the residue of a substituted or unsubstituted aliphatic, cycloaliphatic or aromatic dicarboxylic acid.

3. The polyester of claim 2, wherein B is the residue of a substituted or unsubstituted aliphatic dicarboxylic acid of 2–20 carbon atoms.

4. The polyester of claim 3, having the unit formula

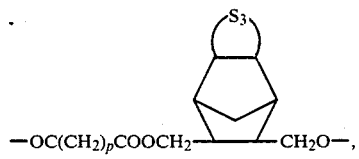

wherein p is 6–14.

5. The polyester of claim 2, comprising an aromatic polyester, wherein B is the residue of a mono-, di- or tricyclic aromatic dicarboxylic acid.

6. The polyester of claim 5, having the unit formula

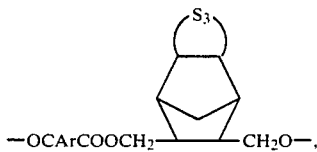

wherein Ar is the residue of phthalic, isophthalic or terephthalic acid.

7. A polymer of claim 2, comprising a polyester crosslinked by reaction through the trithia substituent and having the unit formula

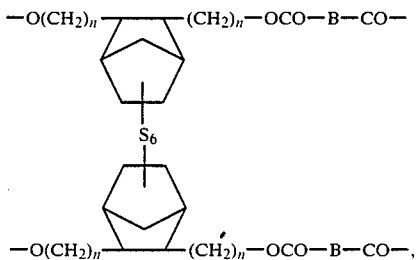

wherein the trithiatricyclo[5.2.1.0$^{2,6}$]decane is substituted or unsubstituted.

8. A polymer of claim 1, comprising a polyurethane, wherein D is the residue of a substituted or unsubstituted aliphatic, cycloaliphatic or aromatic diisocyanate.

9. A polyurethane of claim 8, wherein D is the residue of a substituted or unsubstituted aliphatic diisocyanate of 4–20 carbon atoms.

10. The polyurethane of claim 9, having the unit formula

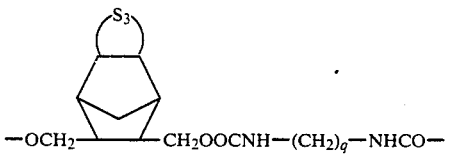

wherein q is 4–12.

11. The polyurethane of claim 8, wherein D is the residue of a mono-, di- or tricyclic aromatic diisocyanate.

12. The polyurethane of claim 11, having the unit formula

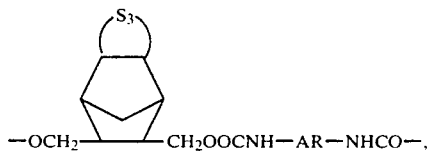

wherein AR is the residue of toluene diisocyanate, phenylene diisocyanate or methylenebis(phenylisocyanate).

13. A polymer of claim 8, comprising a polyurethane crosslinked by reaction through the trithia substituent and having the unit formula

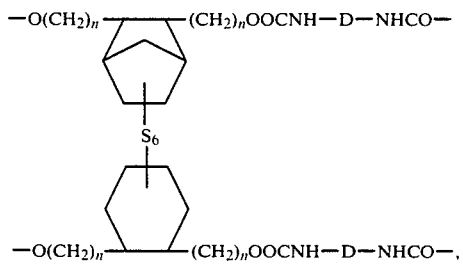

wherein the trithiatricyclo[5.2.1.0$^{2,6}$]decane is substituted or unsubstituted.

14. The polyurethane of claim 8, crosslinked by reaction between an available hydroxyl group and triisocyanate or by reaction between an available isocyanate group and a triol or triamine.

15. The polymer of claim 1, comprising an epoxy composition, wherein E is the residue of a substituted or unsubstituted aliphatic, cycloaliphatic or aromatic dihydroxylic chain extender for a diglycidyl ether of the trithiatricyclo[5.2.1.0$^{2,6}$]decane.

16. The epoxy composition of claim 15, wherein the dihydroxylic chain extender is a bis(hydroxyalkyl)trithiatricyclo[5.2.1.0$^{2,6}$]decane.

17. The epoxy composition of claim 15, wherein the dihydroxylic chain extender is bisphenol A.

18. A polymer of claim 15, comprising a polyepoxy composition crosslinked through the trithia substituent and having the unit formula

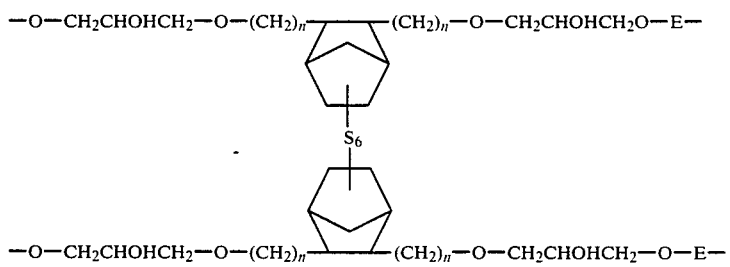

wherein the trithiatricyclo[5.2.1.0$^{2,6}$]decane is substituted or unsubstituted.

19. A polyepoxy composition of claim 15, crosslinked by reaction with a trifunctional amine.

20. A process for the preparation of a substituted or unsubstituted 8,9-bis(hydroxymethyl)-exo-3,4,5-trithiatricyclo[5.2.1.0$^{2,6}$]decane comprising the steps of:

(a) reducing a precursor nadic anhydride or substituted nadic anhydride to a corresponding substituted or unsubstituted 5,6-bis(hydroxymethyl)bicyclo[2.2.1]hept-2-ene and (b) sulfurizing an olefinically unsaturated bond at the 2-position of the thus-produced 5,6-bis(hydroxymethyl)bicyclo[2.2.1]hept-2-ene to produce a corresponding substituted or unsubstituted 8,9-bis(hydroxymethyl)-exo-3,4,5-trithiatricyclo[5.2.1.0$^{2,6}$]decane.

21. The process of claim 20, wherein the nadic anhydride is unsubstituted and the product is 8,9-bis(hydroxymethyl)-exo-3,4,5-trithiatricyclo[5.2.1.0$^{2,6}$]decane.

22. The process of claim 20, wherein the precursor nadic anhydride or substituted nadic anhdride is reduced with lithium aluminum hydride and wherein the olefinically unsaturated bond at the 2-position of the thus-produced hept-2-ene precursor is sulfurized in the presence of an alkali metal sulfide catalyst.

* * * * *